United States Patent [19]

Nagy et al.

[11] Patent Number: 4,477,771
[45] Date of Patent: Oct. 16, 1984

[54] MICROWAVE DETECTION OF SOOT CONTENT IN A PARTICULATE TRAP

[75] Inventors: Louis L. Nagy, Warren; David S. Eddy, Romeo; Michael J. O'Rourke, Sterling Heights, all of Mich.

[73] Assignee: General Motors Corporation, Detroit, Mich.

[21] Appl. No.: 390,406

[22] Filed: Jun. 21, 1982

[51] Int. Cl.³ .......................................... G01R 27/04
[52] U.S. Cl. ................................................. 324/58.5 C
[58] Field of Search .................................. 324/58.5 C

[56] References Cited

U.S. PATENT DOCUMENTS 4,042,879 8/1977 Ho et al. ..................... 324/58.5 C
4,369,404 1/1983 Flygare et al. .............. 324/58.5 C

FOREIGN PATENT DOCUMENTS 1302380 1/1973 United Kingdom ........... 324/58.5 C

Primary Examiner—Stanley T. Krawczewicz
Attorney, Agent, or Firm—Warren D. Hill

[57] ABSTRACT

Conductive particulates in the form of soot are collected from diesel engine exhaust gases on a porous wall monolithic ceramic filter in such a way that the soot is somewhat uniformly distributed throughout the filter. The filter is housed in a chamber having a property of a microwave resonant cavity and the cavity is excited with microwave energy. As the particulates are collected the cavity appears to the microwaves to have an increasing dielectric constant even though the matter being accumulated is conductive rather than dielectric so that as collected on the porous filter it has the property of an artificial dielectric. The response of the cavity to the microwave energy is monitored to sense the effect of the dielectric constant of the material within the cavity to provide a measure of the soot content in the filter.

3 Claims, 4 Drawing Figures

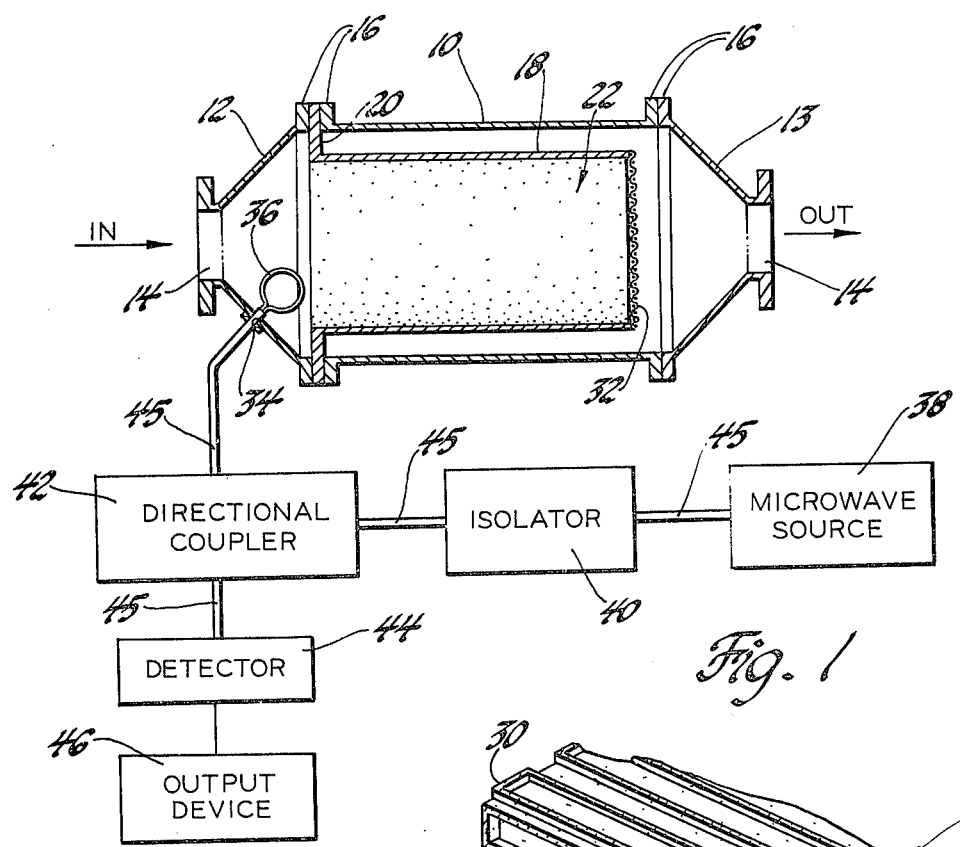
Fig. 1
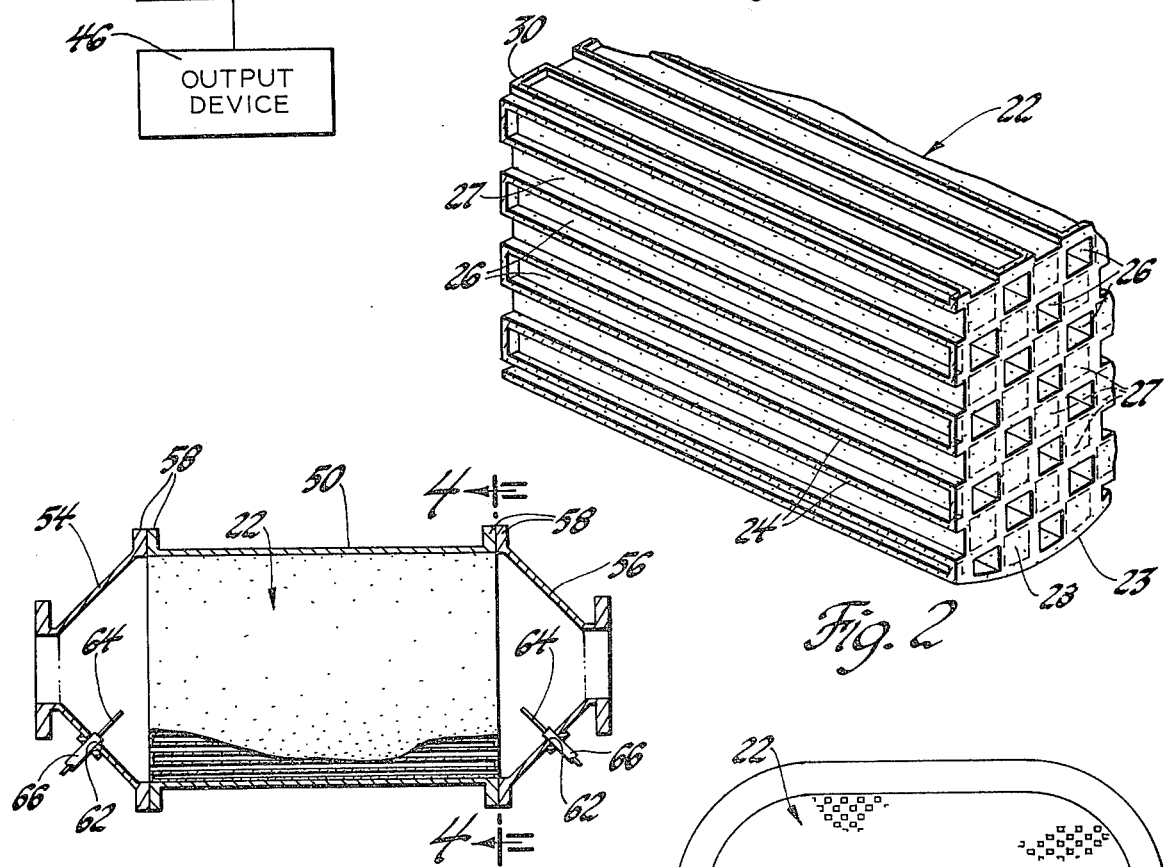
Fig. 2
Fig. 3
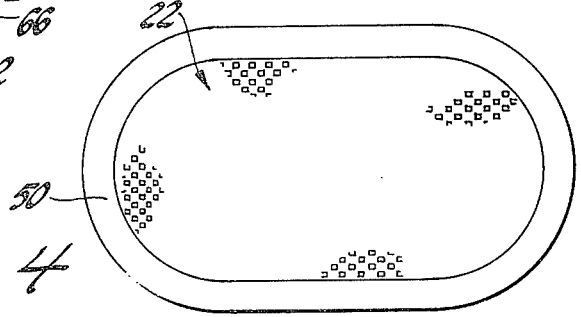
Fig. 4

MICROWAVE DETECTION OF SOOT CONTENT IN A PARTICULATE TRAP

This invention relates to the detection of accumulated soot particulates in a diesel engine exhaust filter and more particularly to a microwave method for detecting the accumulation of such particulates.

To remove particulates which primarily comprises soot coated with hydrocarbons from the exhaust gases of a diesel engine a filter is interposed in the engine exhaust pipe. It is necessary to periodically remove the particulates by replacing the filter or by incineration so that excessive loading of the filter by the particulates does not impede the gas flow through the filter. It is desired to cause an incineration when substantial accumulation has occurred but before the accumulation is so great that the incineration would generate excessive temperatures. Accordingly, some way of determining when the incineration should occur is needed.

Techniques for measuring the dielectric constant of dielectric materials in a cavity are well known and are used to determine the amount of a dielectric material in a container or the amount of one dielectric material that is mixed with another, e.g. oil in water. The measurement of the amount of diesel exhaust particulates in a filter medium presents the problem of detection since the particulates primarily comprise soot which is conductive. One would not expect that the dielectric constant measurement method would be useful for the measurement of conductive material. It has been discovered, however, that if the conductive particulates can be collected on a dielectric filter medium in such a way that they are substantially uniformly dispersed throughout the medium, then the filter resembles an artificial dielectric and the effective dielectric constant increases as the accumulation of conductive particulates increases.

It is, therefore, an object of this invention to provide a method of detecting soot accumulation in a diesel exhaust particulate filter. It is a further object of the invention to provide such a method utilizing microwaves to detect the soot accumulation in such a filter.

The invention is carried out by collecting conductive particulates from diesel exhaust gases on a dielectric filter medium in a chamber having the property of a microwave resonance cavity wherein the particulates are collected in a pattern uniformly dispersed throughout the resonance cavity so that the dielectric loading of the cavity increases with increasing particulate content, and then exciting the cavity with microwave energy and monitoring the response of the cavity to sense the effective dielectric constant of the material in the cavity thereby providing a measure of the particulate content in the filter. In particular the method is applied to a filter which defines a plurality of parallel passages separated by porous walls wherein alternate passages are blocked at one end and the remaining passages are blocked at the other end so that exhaust gases flow through the porous walls and the particulates are collected on the porous walls.

These and other features and advantages of the invention will be more fully understood from the following description and the accompanying drawings wherein:

FIG. 1 is a cross-sectional view of a diesel exhaust particulate trap adapted for microwave detection of the soot accumulation coupled with a block diagram of a microwave circuit for carrying out the method of the invention, FIG. 2 is a sectional pictorial view showing the construction of a monolithic ceramic filter element used in the particulate trap of FIG. 1, FIG. 3 is a cross-sectional view of another embodiment of a filter trap fitted for a microwave detection according to the invention, and FIG. 4 is a cross-sectional view along line 4—4 of FIG. 3.

Referring to FIG. 1, a particulate trap for a diesel engine exhaust comprises an outer cylindrical steel housing 10 fitted at the ends with frusto-conical reducing housing end sections 12 and 13 with central openings 14 for connection with the inlet and outlet exhaust pipes, not shown. The end sections 12 and 13 are coupled to the outer housing 10 by flanges 16. A steel inner housing 18, also cylindrical, and spaced from the outer housing by an annular gap is supported by a flange 20 at one end which is joined to one set of flanges 16 on the outer housing.

Within the housing 18, there is disposed a high efficiency incineration cleanable ceramic filter element which may have any of a number of possible configurations such as, for example, that of the element illustrated in FIG. 2 and generally indicated by numeral 22. Filter element 22 is in the form of a ceramic monolith having a surrounding cylindrical outer wall 23 internally interconnected by a large number of interlaced thin porous internal walls 24. The interlaced walls define internally thereof two groups of parallel passages including respectively inlet passages 26 and outlet passages 27, each extending to opposite ends of the element 22. The inlet passages 26 are open at the inlet end 28 of the element and are closed at the outlet end 30 of the element, while the outlet passages 27 are closed at the element inlet end 28 and open at the outlet end 30.

In the FIG. 2 embodiment, the passages are of square cross section although numerous other configurations could be utilized. Further, the inlet and outlet passages are arranged in vertical and horizontal rows (as viewed in cross section) with the inlet passages alternating with exhaust passages in a checkerboard pattern. Thus, it will be appreciated that each interior wall portion of the element lies between an inlet passage and an outlet passage at every point of its surface except where it engages another wall, as it does at the corners of the passages. So, except for the corner engagement, the inlet passages are spaced from one another by intervening outlet passages and vice versa.

The construction of the ceramic monolith is such that the interior walls 24 are porous so as to permit passage of exhaust gases through the walls from the inlet to the outlet passages. The porosity of the walls is sized appropriately to filter out a substantial portion of the particulates present in diesel exhaust gases. Tests have indicated that efficient filtration is provided by a ceramic wall structure having an average porosity of about 10%, a mean pore size of from about 2 to 15 microns in a range or pore sizes of from about 0.5 microns to about 70 microns. This has been accomplished in a monolith structure having square passages measuring on the average about 0.06 inches on a side with a wall thickness of about 0.015 inches between passages. Recognizing that the entire internal wall structure between inlet and outlet passages represents active filtering area, it is apparent that this structure provides more than 20 square inches of filter wall area for each cubic inch of the monolithic filter structure. Thus, a filter having very low restriction with a large amount of filter area in a very small package is provided. Increasing the average porosity of the walls above the 10% figure of the initial test samples would, of course, be expected to further reduce the restriction to gas flow through the filter element, at least to a point where the areas of the inlet and outlet passages become the limiting factors to gas flow.

In operation of an engine having one or more of the described compact high-efficiency exhaust particulate filter elements in the exhaust system, exhaust gases will be passed from the engine into the particulate trap 16 where they enter the filter element through the open ends of the inlet passages at the inlet end 28 of the element. The incoming gases are distributed throughout the lengths of the respective inlet passages from which they pass through all of the porous walls defining the respective passages into the adjacent outlet passages.

A large portion of the carbonaceous particulates in the diesel exhaust gases are trapped and collected on the interior surfaces of the inlet passage walls as the exhaust gases pass therethrough. The collected particulates form a cake on the wall surfaces which build up until it eventually reaches a thickness that begins to interfere with gas flow through the walls. The cleaned gases, passing through the walls into outlet passages, continue to their open ends at the outlet end of the element and continue through the remainder of the exhaust system to the atmosphere.

Periodically, during operation of an engine with an exhaust filter of the type described, the collected particulates will reach a level beyond which the restriction to gas flow will become excessive. At or in advance of this point, it becomes necessary to either clean or replace the filter element so that efficient operation of the engine in the vehicle may continue. While the high efficiency compact monolithic ceramic element 22 is capable of use in any desired manner, it is intended that cleaning of the element will best be accomplished through heating the element to a temperature at which the collected particulates are incinerated by reaction with oxygen in the exhaust gas stream. Such incineration can take place by heating of the exhaust gases during engine operation to the desired incineration temperature, subject of course to suitable methods of heating and control of combustion temperatures.

Further details on the construction and operation of such a ceramic filter may be found in the Outland, U.S. Pat. No. 4,276,071.

Referring again to FIG. 1, the downstream end of the housing 18 is spanned by an RF shorting screen 32 comprising a coarse metal mesh welded to the steel housing 18 and serving to prevent the passage of microwaves through the downstream end of the housing while allowing the free passage of the exhaust gases. The front section 12 of the trap housing contains an aperture 34 through which a loop-type microwave probe 36 is inserted thereby positioning the probe 36 at the upstream end of the filter element. The cylindrical metallic filter housing 18 shorted at one end by screen 32 and closed by the front section 12 at the other end serves as a microwave resonance cavity which is excited according to the excitation of the microwave probe 36. The same probe picks up the reflected microwave in the cavity and provides a corresponding output signal. The resonant frequency of the cavity is dependent upon its physical geometry, the electrical properties of the material within it and the order of mode excited. It has been discovered that the filter and the soot accumulated therein can be modeled as an artificial dielectric whose permittivity increases with soot content. The theory of artificial dielectrics is discussed by J. D. Kraus, *Electromagnetics*, McGraw-Hill Book Company, Inc., New York, 1953, pages 56–59. According to that theory, discrete metal particles of macroscopic size dispersed throughout a dielectric material increases the permittivity of that material according to the particle size and the number of particles per unit volume of the material. Ideally, according to artificial dielectric theory, the spacing between particles is much less than a wavelength and their diameters are much less than their spacing. In practice, the soot particles, coated with hydrocarbons, are collected in thick layers on the filter walls and hence are packed close to one another. Thus the classical artificial dielectric theory does not predict the behavior of the soot loaded filter. However, experimental evidence shows that the conductive soot particles collected on the porous walls of the ceramic filter 22 are dispersed sufficiently uniformly throughout the volume of the filter so that the filter behaves like an artificial dielectric and its permittivity increases as the soot accumulation increases. That permittivity or dielectric constant then can be measured by microwave techniques and, in particular, since the dielectric loading of the material within a resonant chamber affects the resonant frequency of the chamber that phenomena can be used to measure the effective dielectric constant and the soot content of the filter. The effect of the soot accumulation on the resonant frequency of the resonant chamber has been measured. The housing 18 containing the filter element 22 was about 6 inches in diameter and 7 inches long. The opening 14 in the front end section 12 was 4 inches from the end of the housing 18. It was found that a linear decrease of frequency occurs as the particulate content increases. At a nominal resonant frequency of 1.85 GHz the resonant frequency shifts at a rate of 1.7 MHz per gram of particulate accumulated on the filter. The hydrocarbon coating on the soot particles affects the dielectric constant by an amount two orders of magnitude less than the soot so its contribution to the measurements is insignificant.

To excite the resonant chamber containing the filter 22 a microwave source 38 is coupled through an isolator 40 and a directional coupler 42 to the loop-type microwave probe 36. A diode detector 44 connected to the directional coupler 42 senses the magnitude of the signal reflected back by the probe 36. All of these microwave elements 36–44 are connected by coaxial cable or other waveguides 45. The output of the detector 44 is electrically connected to an output device 46 which may be a meter calibrated to indicate the relative dielectric constant of the loaded filter 22 or the percentage of allowed maximum soot accumulation. The output device 46 may also comprise a telltale lamp or alarm indicating when the limit of soot accumulation has been reached. Preferably the output device will signal an automatic regeneration or incineration device to ignite the soot during engine operation to clean the filter 22 by incineration. Incineration techniques which may be triggered by an electrical signal are already known. See, for example, the Ludecke et al U.S. Pat. No. 4,211,075.

One mode of operation of the microwave system of FIG. 1 is to establish a fixed frequency for the microwave source 38 which is the frequency for the resonant condition of the chamber when the filter 22 is loaded with particulates to its maximum desired accumulation, and then by means of the detector 44, to sense a null in the reflected signal which occurs at the resonant condition. When the filter 22 is clean the detector output signal is large and as the particulates accumulate in the filter the effective relative dielectric constant of the material in the resonant chamber increases and the detector output decreases until it reaches its lowest value at the resonant condition. By providing the output device 46 with a voltage detector circuit set to respond to a preset low detector output representing the resonant condition, the device 46 is enabled to signal that the maximum soot load has been accumulated or to trigger the incineration cycle for cleaning the filter. An alternate mode of operation varies the microwave frequency through a range representing the resonant frequencies of the resonant chamber for the various values of dielectric loading encountered during engine operation. Then by determining the frequency for which a null occurs at any point in time, the amount of dielectric loading of the resonant chamber is determined. This is useful if the condition of the filter is to be checked at times other than when the maximum particulate loading has occurred. This may be done, for example, when the incineration process has occurred and it is desired to ascertain whether a complete cleaning of the filter has in fact taken place.

The reflectance technique of monitoring the cavity resonance condition, as illustrated in FIG. 1, is not the only way of carrying out the method of the invention. FIGS. 3 and 4 illustrate another particulate filter design in which a transmission type measurement is made to sense the resonant condition of the filter. There a steel housing 50 of flattened oval cross section is filled with the ceramic filter medium 22 of the kind described and two housing end sections 54 and 56 are joined at flanges 58 to the housing 50. The end sections are tapered outwardly to apertured and flanged fittings adapted to connect to diesel engine exhaust pipes, not shown. Each of the sections 54 and 56 are provided with ports 62 through which straight wire microwave probes 64 are inserted. Each probe being connected to a coaxial cable 66 which would lead, respectively, to a microwave source and to a microwave detector, not shown. Unlike the arrangement of FIG. 1, there is no RF shorting screen across an end of the filter 22 so as to allow microwave propogation through the entire chamber defined by the housing and end sections so that the signal emitted by the one probe 64 will reach the other. The apertures in the end sections 54 and 56 are small enough to contain the microwave radiation within the housing. Thus, the housing configuration which defines the geometry of the resonant chamber is not critical but can take many forms and the resonance measuring technique likewise is not limited to one particular kind but also can incorporate the various practices known in the art for monitoring resonant conditions or otherwise monitoring the relative dielectric constant of the loaded filter material. The filter material itself is not limited to the one kind described herein but rather can take many forms so long as the pattern of hydrocarbon coated soot particle deposition is such that the soot dispersion throughout the filter media is sufficiently uniform to be modeled as an artificial dielectric.

It will thus be seen that according to the method of this invention if particulate conductive material is sufficiently uniformly collected throughout a filter media so that the resultant dispersion resembles an artificial dielectric then microwave dielectric constant measuring techniques can be used to detect the accumulation of the conductive particulates. This remains true in the case of hydrocarbon coated soot particulates even where the particulates are collected in thick layers on the filter walls. In particular the techniques for measuring the resonance of microwaves within a chamber can be used to monitor the change of effective dielectric constant.

The embodiments of the invention in which an exclusive property or privilege is claimed are defined as follows:

1. The method of detecting the accumulation of conductive particulates being collected from diesel engine exhaust gases on a collection medium formed of dielectric material in a chamber having the property of a microwave resonance cavity, comprising the steps of:
   collecting particulates on the medium in a pattern substantially uniformly dispersed throughout the cavity whereby the dielectric loading of the cavity increases with increasing conductive particulate content,
   exciting the cavity with microwave energy, and
   monitoring the response of the cavity to the microwave energy to sense the effective dielectric constant of the material within the cavity thereby providing a measure of the conductive particulate content in the collection medium.

2. The method of detecting the accumulation of conductive particulates being collected from diesel engine exhaust gases on a collection medium formed of dielectric material in a chamber having the property of a microwave resonance cavity, comprising the steps of:
   collecting particulates on the medium in a pattern sufficiently uniformly dispersed throughout the cavity to resemble an artificial dielectric whereby the dielectric loading of the cavity increases with increasing conductive particulate content,
   exciting the cavity with microwave energy, and
   monitoring the response of the cavity to the microwave energy to sense the effective dielectric constant of the material within the cavity thereby providing a measure of the conductive particulate content in the collection medium.

3. The method of detecting the accumulation of conductive particulates being collected from diesel engine exhaust gases on a honeycomb filter formed of dielectric material in a chamber having the property of a microwave resonance cavity, the filter defining a plurality of parallel passages separated by porous walls having alternate passages blocked at one end and the remaining passages blocked at the other end so that exhaust gases flow through the porous walls, comprising the steps of:
   collecting particulates on the porous walls in a pattern sufficiently uniformly dispersed throughout the cavity to resemble an artificial dielectric whereby the dielectric loading of the cavity increases with increasing conductive particulate content,
   exciting the cavity with microwave energy, and
   monitoring the response of the cavity to the microwave energy to sense the effective dielectric constant of the material within the cavity thereby providing a measure of the conductive particulate content in the collection medium.

* * * * *